US011835405B2

(12) United States Patent
Neumann et al.

(10) Patent No.: US 11,835,405 B2
(45) Date of Patent: Dec. 5, 2023

(54) FORCE MEASURING DISC AND DEVICE FOR DETERMINING FORCES IN THE PICO-NEWTON TO NANO-NEWTON RANGE

(71) Applicant: Universitaet Heidelberg, Heidelberg (DE)

(72) Inventors: Hendrikje Neumann, Koblenz (DE); Christine Selhuber-Unkel, Kiel (DE); Eckhard Quandt, Heikendorf (DE)

(73) Assignee: Universitaet Heidelberg, Heidelberg (DE)

( * ) Notice: Subject to any disclaimer, the term of this patent is extended or adjusted under 35 U.S.C. 154(b) by 0 days.

(21) Appl. No.: 17/638,961

(22) PCT Filed: Aug. 16, 2020

(86) PCT No.: PCT/DE2020/100712
§ 371 (c)(1),
(2) Date: Feb. 28, 2022

(87) PCT Pub. No.: WO2021/043366
PCT Pub. Date: Mar. 11, 2021

(65) Prior Publication Data
US 2022/0291063 A1 Sep. 15, 2022

(30) Foreign Application Priority Data

Sep. 2, 2019 (DE) ..................... 10 2019 123 394.1

(51) Int. Cl.
*G01L 1/24* (2006.01)
*G01N 33/483* (2006.01)
(52) U.S. Cl.
CPC ............ *G01L 1/24* (2013.01); *G01N 33/4833* (2013.01)

(58) Field of Classification Search
CPC .............................. G01L 1/24; G01N 33/4833
(Continued)

(56) References Cited

U.S. PATENT DOCUMENTS 6,935,759 B1 * 8/2005 Staker .................. B81B 3/0062
359/872
9,487,388 B2 * 11/2016 Brosh ....................... G01L 1/18
(Continued)

FOREIGN PATENT DOCUMENTS

DE 102010012701 A1 11/2011
WO 2019010234 A1 1/2019

OTHER PUBLICATIONS

International Search Report dated Nov. 5, 2020, in International Application No. PCT/DE2020/100712.
(Continued)

*Primary Examiner* — Nathaniel T Woodward
(74) *Attorney, Agent, or Firm* — Stephan A. Pendorf; Patent Central LLC

(57) ABSTRACT

A force measuring plate having a planar regular arrangement of force measuring cells. A force measuring cell is formed in a hole in the force measuring plate, in which hole precisely one planar element which is secured by springs in a self-supporting fashion is arranged and is oriented so as to run parallel to the force measuring plate. Each spring is connected in a materially joined fashion at a first end to the edge of a hole and at a second end to the edge of a planar element. The force measuring plate, the springs and the planar elements are formed from the same material. Each planar element can be elastically deflected in three spatial directions under the effect of a force. There is a linear relationship between the deflection and the force. In addition, the invention relates to a device for determining forces in the piconewton to nanonewton ranges.

16 Claims, 4 Drawing Sheets

(58) Field of Classification Search
USPC .................................................. 73/862.637
See application file for complete search history.

(56) References Cited

U.S. PATENT DOCUMENTS

| | | | |
|---|---|---|---|
| 2005/0126287 A1* | 6/2005 | Malametz | G01P 15/125 |
| | | | 73/514.32 |
| 2005/0160816 A1* | 7/2005 | Yu | B81C 3/002 |
| | | | 73/514.29 |
| 2010/0147076 A1* | 6/2010 | Diamond | B81C 1/00246 |
| | | | 73/514.32 |
| 2014/0352447 A1* | 12/2014 | Yoshikawa | G01L 1/18 |
| | | | 73/774 |
| 2017/0184628 A1 | 6/2017 | Hsu et al. | |
| 2017/0322193 A1 | 11/2017 | Gather et al. | |
| 2022/0306451 A1* | 9/2022 | Webb | A61M 37/0015 |

OTHER PUBLICATIONS

Genki Yoshikawa, et al. "Nanomechanical Membrane-type Surface Stress Sensor", Nano Letters, US, vol. 11, No. 3, Mar. 9, 2011 (Mar. 9, 2011), pp. 1044-1048, DOI: 10.1021/nl103901a, ISSN: 1530-6984, XP055506585, the whole document.

Solgaard Olav, et al. "Optical MEMS: From Micromirrors to Complex Systems", Journal of Microelectromechanical Systems, IEEE Service Center, US, vol. 23, No. 3, Jun. 1, 2014 (Jun. 1, 2014), pp. 517-538, [retrieved on May 29, 2014], Doi: 10.1109/JMEMS.2014.2319266, ISSN: 1057-7157, XP011549786, the whole document.

* cited by examiner

FORCE MEASURING DISC AND DEVICE FOR DETERMINING FORCES IN THE PICO-NEWTON TO NANO-NEWTON RANGE

BACKGROUND OF THE INVENTION

Field of the Invention

The invention relates to a force measuring plate having a planar, regular arrangement of force measuring cells, with a force measuring cell being formed in a hole in the force measuring plate, in which exactly one planar element secured by springs in a self-supporting fashion is arranged and aligned parallel to the force measuring plate.

The invention also relates to a device for determining forces in the pico-Newton to nano-Newton range.

The invention could also be referred to as a mechano-optical submicronewton 3D dynamometer or microsensor system, but this is not to be considered limited thereto.

This new type of microsensor system, or the force measuring plate, enables 3D force measurements in the pico to micronewton range, especially for micrometer-sized adhesive samples and living systems such as cells or bacteria.

Description of the Related Art

In times of rapid developments and growing markets in the field of robotics, with a special focus on humanoid robots, high-tech prosthetics and personalized medicine, the biomimetics of natural materials such as artificial skin is of central interest in research and industry. In order to comprehensively understand the structure-function relationships in living systems, the extensive expansion of knowledge in relation to the smallest living building block, the cell, and its biomechanics is the subject of ongoing research projects worldwide. However, until now there has not been a comprehensive established method that can quantitatively measure 3D cell forces, for example during the cell migration process.

In recent years, various methods have been developed in a variety of studies to gain a more detailed insight into cell mechanics. Of particular interest was the electrochemical sensor technology of cells through external stimuli, the so-called mechanotransduction, which causes macroscopic phenomena such as wound healing through cell migration. To manipulate or mimic these dynamic cellular processes in future applications, cellular forces have been recorded using a variety of techniques such as atomic force microscopy, microelectromechanical systems (MEMS), micropillar array deformation, or tensile force microscopy, among others. However, none of the previously established techniques enabled a quantitative cell tensile force measurement in the pico- to nanonewton range in three dimensions at once using an inexpensive setup.

Various techniques for cell force measurement in one, two and three dimensions are available and some are already in use. However, the current methods have at least one major disadvantage, such as a limited force range, limitation to one or two dimensions, recording only qualitative measurement results, limited force resolution due to sensor element dimensions that are larger than the cell dimension, and further high complexity or expense of the arrangement.

The cell force measurement using polydimethylsiloxane (PDMS) microcolumns is based, for example, on a significant deformation of the columns as a function of the cell force interaction. This method can only capture forces in two dimensions. Furthermore, the homogeneity of elasticity across the entire PDMS substrate depends on the homogeneity of the polymerization process. This process can vary over the entire sample surface. Another widely used technique is transaction force microscopy (TFM), which is based on the deformation of a hydrogel membrane by cellular forces and computational trajectory analysis of the forces acting on the membrane. The disadvantage here is that the TFM is very time-consuming and expensive and sensitive to inhomogeneities in the hydrogel. Furthermore, the resolution of this technique depends on the softness of the hydrogel, and the softness of the hydrogel affects cell behavior. Therefore, variations in the behavior of elastic materials cause uncertainties in the resulting force data.

Microelectronic systems (MEMS) used for cellular force sensing only allow for two-dimensional force sensing and qualitative force data. Three-dimensional measurements require the combination of at least two different physical phenomena such as piezoresistance and capacitance, which lead to an increase in the dimension of the sensor element.

The publications US 2017/322193 A1 and WO 2019/010234 A1 are mentioned as relevant patent documents that deal with exactly the same task. The approach of both documents corresponds roughly to the following, namely that each device respectively is disclosed for determining forces, in particular very small forces that occur as adhesion and traction forces in living (animal or human) cells or cell clusters, with the basic idea being to record these forces indirectly by bending or deflecting predetermined and—as far as possible—pre-calibrated test elements. The changes in shape of the test elements are to be recorded optically and then translated into forces exerted by the cells, with the force measuring plate being formed from a soft, thin polymer film (e.g., PDMS) that can be deformed by the cell forces on a rigid, transparent base. The cells lying on the front deform the polymer film and the optical reflectors embedded in the film (micromirrors or optical cavities) are elastically deflected as a result. Here, too, the measurement is carried out by optical interferometry from the back of the polymer film. The main difference is therefore the design of the force measuring plate, which, taken by itself as a component of the overall device, should also be a commercially available product.

It should be noted that it is known per se in MEMS construction, for example, to structure self-supporting surfaces suspended on spring structures in a meandering form from an initially monolithic block of material or, alternatively, to build them up using sputter technology. Meander springs are used in particular in micro force sensors (cf. DE 10 2010 012 701 A1).

In the course of this invention, a novel, surface-integrated, mechano-optical microsensor system was conceived, designed, prototyped and tested, which enables the measurement of pico- to micronewton-small tensile forces simultaneously in three dimensions. In this system, the displacement of a sensor element with a well-defined structure is directly correlated with a specific force by previously determining the force constants for each spatial direction.

The 3D force sensor system should be able to perform simultaneous quantitative three-dimensional force measurements and, in particular, it should also simultaneously record the state of the sensor element before, during and after the measurement.

BRIEF SUMMARY OF THE INVENTION

The object or task of the invention is solved with a force measuring plate according to the main claim and a device for determining forces in the pico-Newton to nano-Newton range according to the subordinate claim. Further advantageous configurations can be found in the dependent claims.

The force measuring plate according to the invention has a planar, regular arrangement of force measuring cells, wherein each force measuring cell is formed in a hole in the force measuring plate, in which exactly one planar element secured by springs in a self-supporting fashion is arranged and aligned parallel to the force measuring plate, each spring materially joined at a first end with an edge of a hole and at a second end to an edge of a planar element, wherein a. the force measuring plate, the springs and the planar elements are made of the same material,
    b. the springs as formed as elongated meander structures with more than two meander periods and
    c. each planar element is surrounded by four springs arranged rotationally symmetrical and
    d. each planar element is elastically deflectable in three spatial directions under the action of a force, with deflection and force being in a linear relationship.

Furthermore, the structural thickness of planar elements and springs can be set to be less than 500 nanometers or less than 200 nanometers.

Furthermore, it is advantageous to set the structure width of the meanders to less than 2 micrometers.

It is advantageous if the diameter of the force measuring cells is set to be less than 200 micrometers.

It is also advantageous if the force measuring plate is made of a biocompatible material, preferably made of a nickel-titanium alloy or made of amorphous silicon.

The arrangement of the force measuring cells can be aligned along two mutually perpendicular axes.

In particular, the elongated meander structures can be aligned along the same axes that determine the arrangement of the force measuring cells.

It is advantageous if the hole in the force measuring plate assigned to a force measuring cell is circular.

The planar elements can be mirrored on a predetermined flat side.

Furthermore, the planar elements can carry a functional layer on the flat side opposite the mirror coating.

The material of the force measuring plate has in particular a modulus of elasticity in the interval from 1 to 80 GPa.

The ratio of the diameters of the holes in the force measuring plate to the diameters of the planar elements can be approximately 10:1.

According to the invention, the device for determining forces in the pico-Newton to nano-Newton range comprises at least one force measuring plate according to the invention as well as means for optically measuring the three-dimensional deflections of the planar elements of the at least one force measuring plate.

The device can also additionally have an electronic translation device, designed to extrapolate the forces acting on the planar elements from the measured deflections.

BRIEF DESCRIPTION OF THE SEVERAL VIEWS OF THE DRAWINGS

Further advantages, features and applications of the present invention will become apparent from the following description taken in conjunction with the figures. There is shown in.

DETAILED DESCRIPTION OF THE INVENTION

Figure 1:
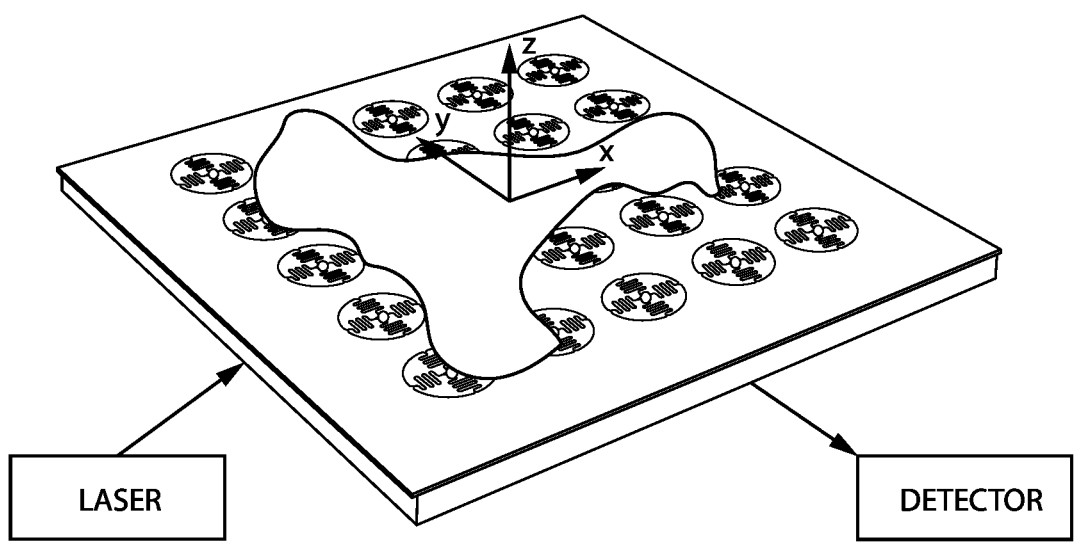
FIG. 1 a functional model of a novel surface-integrated mechanical-optical microsensor system, FIG. 2A, B, B1 free-standing sensor elements developed using topography and finite element analysis for maximum performance and sensitivity, FIG. 3 3D DEM images for different displacement states of the NiTi sensor element shown in FIG. 2A, and FIG. 4A, B a schematic representation of a DHM/DIC setup (A), which serves as an example as an add-on setup in combination with an AFM (B) for local and global 3D force measurement of cells.

In particular, the invention provides for the design of a force measuring disc made of a material that is initially inflexible compared to the cells (hereafter "inflexible material" for brevity) (in a preferred embodiment with a modulus of elasticity of 1-80 GPa), which is pre-structured in order to make local planar elements sensitive for small forces in the pico to nano Newton range. Particular importance is attached to the fact that the deflection of each planar element in three dimensions follows Hook's law, i.e. it is directly proportional to the applied force. In addition, the individual planar elements, which are arranged in an array on the force measuring disc, are mechanically completely decoupled from one another, since the inflexible material between the planar elements does not transmit any forces.

The planar elements are designed as self-supporting structures which are suspended in particular from meander springs and which are machined directly from the inflexible material. The force measuring disc has holes in which the planar elements are elastically mounted. The spring and planar element consist in particular of the same material as the force measuring disc, preferably of a biocompatible nickel-titanium alloy or of amorphous silicon.

The deflections of the planar elements should be able to be detected optically from the back of the pane, while the cells rest on the front. The three-dimensional deflections can be detected optically by means of incident light images (x,y) and interference images (z, phase information). If the three spring constants of all planar elements are known through pre-calibration, the acting forces can be determined without complex modelling. It is important that the planar elements minimize tilt during deflection, because active lighting is required for interferometry and the reflected light has to reach the camera. This is achieved through certain dimensioning parameters.

The special feature of the structures used in the force measuring plate of the invention is, however, to be seen in particular in the fact that a planar element is linearly deflected by the meanders in the same plane (unloaded) in three directions under force loading without at the same time tilting significantly ("tilt").

The state of the sensor elements is recorded continuously, particularly during the measurement.

Exemplary Embodiment

In the initial development of a system model, suitable sensor elements were initially designed using topology optimization and linear static finite element analysis. Here, free-standing sensor elements, which are made up of four spring arms with three loops each, arranged symmetrically, mounted in a frame and connected to a middle plate in the center of the element, showed the best properties with lateral and axial displacements in the nanometer range. These design results were fabricated from biocompatible nickel-titanium (NiTi) and amorphous silicon (a-Si) thin films using established micromachining processes. A minimum sensor element diameter of 45 µm with a layer thickness of 200 nm and a structure size of 1 µm was achieved. Furthermore, a process was developed to produce fully biocompatible, gold-coated polydimethylsiloxane (PDMS) microstructures in membranes. This is the starting point for the production of attractive, inexpensive sensor element arrays with easily variable spring constants by varying the polymer components. Atomic force microscopy cantilever based calibrations of the axial and lateral sensor element force constants were established for future accurate and quantitative tensile force measurements. For the first time, a diamagnetic levitation force calibrator (D-LFC) was used as a suitable calibration method for the sensor elements, the accuracy of which was determined to be 1%. The therewith determined spring constants of the 45 µm small a-Si sensor element are as small as possible with 0.012 N/m out of plane and 4.66 N/m in the plane, while the spring constants of the 170 µm large NiTi sensor element are 0.004 N/m axial and 0.087 N/m lateral.

A setup based on a combination of digital holographic microscopy (DHM) and digital image correlation (DIC) was designed and tested for a cheap, simple, compact, widely variable and sensitive mechano-optical data readout. This readout method enables the smallest possible resolution of displacements of 200 nm. When using the NiTi sensor elements, axial tensile forces in the pico and nanometer range and laterally in the nano to micronewton range can be measured quantitatively.

In order to control the adhesion points of the samples on the sensor element middle plate, a technique was designed and implemented in which ink-jet printing was combined with the established method of diblock copolymer micelle nanolithography (BCML). This enabled fast, accurate, simultaneous micro and nano gold dot printing on smooth, sensitive device surfaces such as sensor elements with user-defined microstructures containing quasi-hexagonal gold nanoparticle patterns. This method enables targeted adhesion and control of the number of adhesion sites for future 3D cell force distribution measurements.

For the first time, a combination of digital holography for out-of-plane displacement measurements and image correlation for in-plane displacement measurements has been combined in one setting to quantitatively measure adhesive forces in three dimensions. In this comparatively simple and inexpensive variant, the cell forces are read out by detecting the displacement of modifiable sensor elements with defined spring constants. Forces of living cells can be captured locally on the cell surface simultaneously in three dimensions. Using a technique conceived and tested in this invention, the number of adhesion sites on the sensor element surface can be controlled via ink jet printed nanodot patterns on the sensor element. In this way, comprehensive mechanical studies for cells of different types, such as cancer or tissue cells, and environmental effects on cell behavior, such as toxic environments, can be performed. In addition, cell-inspired materials can be evaluated directly using the same test parameters that are also used for corresponding measurements on cells. This sensor system could not only be used for 3D force measurements in the submicronewton range, but also for testing the adhesion quality of new biomaterials.

Compared to previous methods, this novel force sensor system enables quantitative adhesion force measurement in the pico to micrometer range in three dimensions and is also completely biocompatible and further modifiable. Accordingly, the force range can be varied depending on the defined task through the choice of sensor element material, size and thickness. The arrangement can be made more compact for future applications and is less expensive and easier to handle than other systems. In addition, performance can be continuously improved by developing future algorithmic codes and by reducing feature size in lithographic processing. Finally, the application can be used as an add-on application for a combination with setups such as atomic force microscopes, for additional measurements of global adhesion forces, or fluorescence microscopes for top-view monitoring of cells during migration. To ensure accurate measurements, the pseudo 3D plots accessible via DHM also enable an evaluation of the condition of the sensor element.

Traction forces of up to 800 pN can be achieved with the manufactured NiTi sensor element. Up to 20 nN out-of-plane and between 17 nN and 0.8 µN in-plane can be solved via this simple, inexpensive, easy-to-handle and extensively modifiable setup. As a result, cellular forces and weak adhesive forces can be perceived in this setting. This can be used for force characterizations such as new biomimetic materials with strong adhesive behavior. In addition, three-dimensional information about the state of the sensor element arrays during the scanning process is provided via pseudo-3D diagrams for further validation and control of data reliability.

This force measurement system can be further improved through developments in micro-manufacturing, optimized algorithms and optical resolution improvements. A further improvement in the structural resolution of the lithographic process opens up the possibility of reducing sensor elements and increasing the sensor array density. According to the International Roadmap of Systems and Devices, the manufacturable dimensions of future electronic devices can be significantly reduced within the next ten years. These developments will drive further miniaturization of the sensor elements.

The rapid development of new, more powerful algorithms in the areas of machine learning, big data acquisition, but also within the society of holography and optics will enable even faster image processing in the future. This enables live monitoring of the sensor force measurement. Finally, further improvements in optics and optical resolution will be relevant for further improvements in the resolution of the novel force sensor system. The extension of a sensor element to an array of sensor elements can be realized with the help of micro lens arrays. This method is already used in the camera industry and could offer the possibility of direct force distribution during dynamic events such as cell migration or cell breakage.

Future accurate force measurements are now assured by the establishment of the currently most appropriate and accessible resilient calibration methods, taking into account the size of the sensing element, the accuracy of the established calibration techniques, and the complexity of handling. They were found to be in good agreement with numerically predicted values simulated by finite element analysis; here, out-of-plane spring constants can be determined by atomic force microscopy cantilever sensor element measurements with an accuracy of about 20%. For in-plane spring constants, a diamagnetic levitation force calibrator (DLFC) proved to be an adequate calibration method with a high accuracy of about 1%. This allows the axial and lateral spring constants of the various sensor elements to be determined.

To control the adhesion on the sensor element center discs for future applications, inkjet printing can or is used to functionalize the sensitive sensor element center discs by custom microdrops. For the cell tests, defined cell binding sites are required on the element surface, which can be controlled via simultaneously printed gold nanodot patterns, which are then biofunctionalized. In this invention, the method for simultaneous high-throughput micro-nanopatterning of the sensor element surfaces has been developed and successfully tested. The non-contact, simple, fast, accurate, inexpensive, reproducible and highly modifiable process of inkjet printing is combined with the established gold nanodot pattern process of block copolymer micelle nanolithography (BCML). This enabled custom micropatterns of 4×4 droplet matrices with a dried droplet diameter in the range of 70 μm on a-SI and NiTi-based surfaces within a printing time of approximately 16 s. On smooth surfaces quasi-hexagonal patterns of gold nanoparticles with an interparticle spacing of approx. 30 nm can be printed within one second and are in very good qualitative agreement with nano-patterns generated by spin coating. This hexagonal nanopattern supports the clear adhesion of cells on the surface of the sensor element.

Exemplary embodiments of the invention are described below with reference to the attached figures, which are intended to explain the invention and are not to be viewed as limiting the scope of protection.

Illustration 1:

A functional model of a novel surface-integrated mechanical-optical microsensor system according to FIG. 1 was designed, constructed and tested, which allows for the simultaneous detection of pico- to nano-Newton tensile forces in three-dimensional pseudo-dimensions, including a continuous check of the sensor element state during the measurement. Here, the displacement of a sensor element with a well-defined structure is directly correlated to a specific force by determining the element spring constant for each spatial direction.

For this reason, sensor elements were developed using topography and finite element analysis for maximum performance and sensitivity. Here, an element consisting of four spring arms with three sets of bends, arranged symmetrically, fixed to a frame and connected in the middle via a sensor element center plate shows the best performance for in- and out-of-plane displacements (see FIGS. 2A and 2B).

FIG. 1 thus shows a schematic representation of the mechanical-optical microsensor system consisting of a biocompatible sensor element arrangement, a laser source with additional optical adjustment and a detector for reading out the force-induced sensor element displacement. Here, the sensor element center plates are biofunctionalized (central points in the middle of each individual sensor element) to control the adhesion of a cell (object above the sensor) to the array for 3D cell adhesion force measurements.

Figure 2:
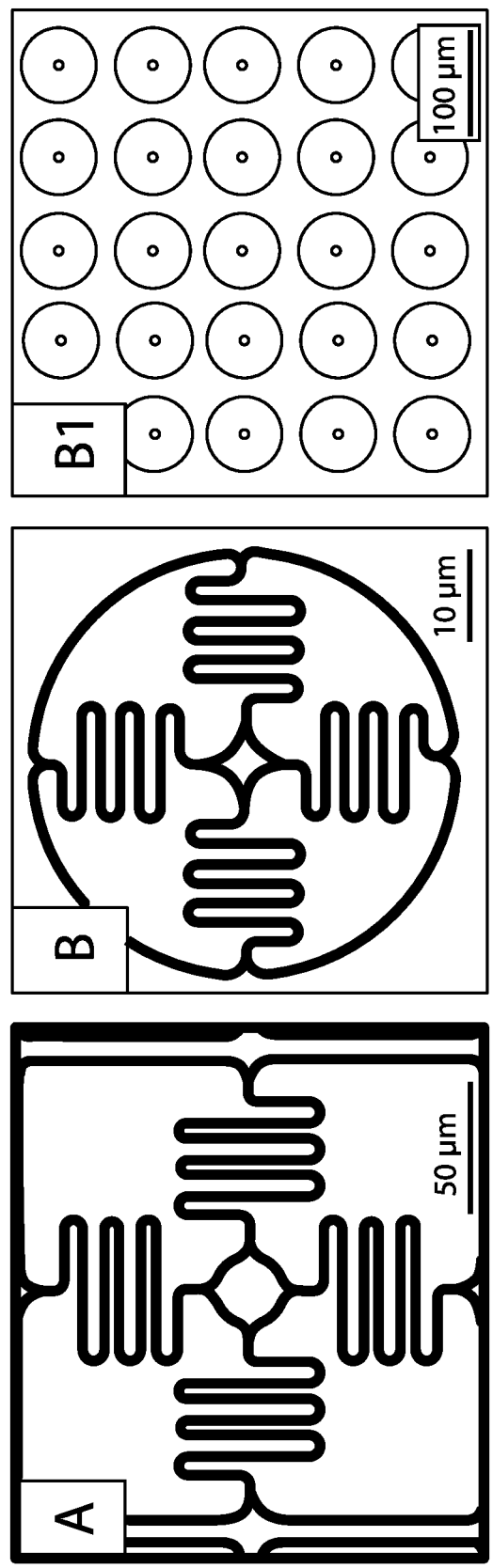

FIG. 2:

FIG. 2 divided into A, B, B1 shows free-standing sensor elements, made by micro-machining A—nickel-titanium (NiTi) with a thickness of 200 nm and an edge length of 170 μm and B—amorphous silicon (a-Si) with a thickness of 200 nm and a minimum diameter of 45 μm. B1—5×5 a-Si micro sensor element array.

Based on these results, 5×5 sensor element arrays (corresponding to FIG. 2 B1) were fabricated from fully biocompatible materials. Wet chemical micromachining was used to fabricate 200 nm thin, stable, free-standing nickel-titanium (NiTi)-based sensor elements with a minimum edge length of 170 μm for foils with a resolution of 2 μm manufactured size (see FIG. 2A).

For future high spatial resolution applications, more compact array designs can be fabricated by dry etching micromachining of amorphous silicon (a-Si). These sensor elements proved to be laterally shiftable by 200% in their original spring arm length. A reduction of the overall sensor element size of 70% compared to the NiTi sensor elements to a minimum sensor element diameter of 45 μm with a device material thickness of 200 nm and a minimum feature size of 1 μm was achieved. In addition, a plasma etching process was developed to produce fully biocompatible, free-standing, gold-plated polydimethylsiloxane (PDMS) structures in membranes with an edge length of at least 1 mm. This is the starting point for the production of attractive, cost-effective sensor arrays with easily tunable spring constants by varying the polymer composition and further reducing the component diameter. In summary, it can be said that biocompatible sensor elements with different mechanical properties can be provided for different force measurement tasks.

Figure 3:
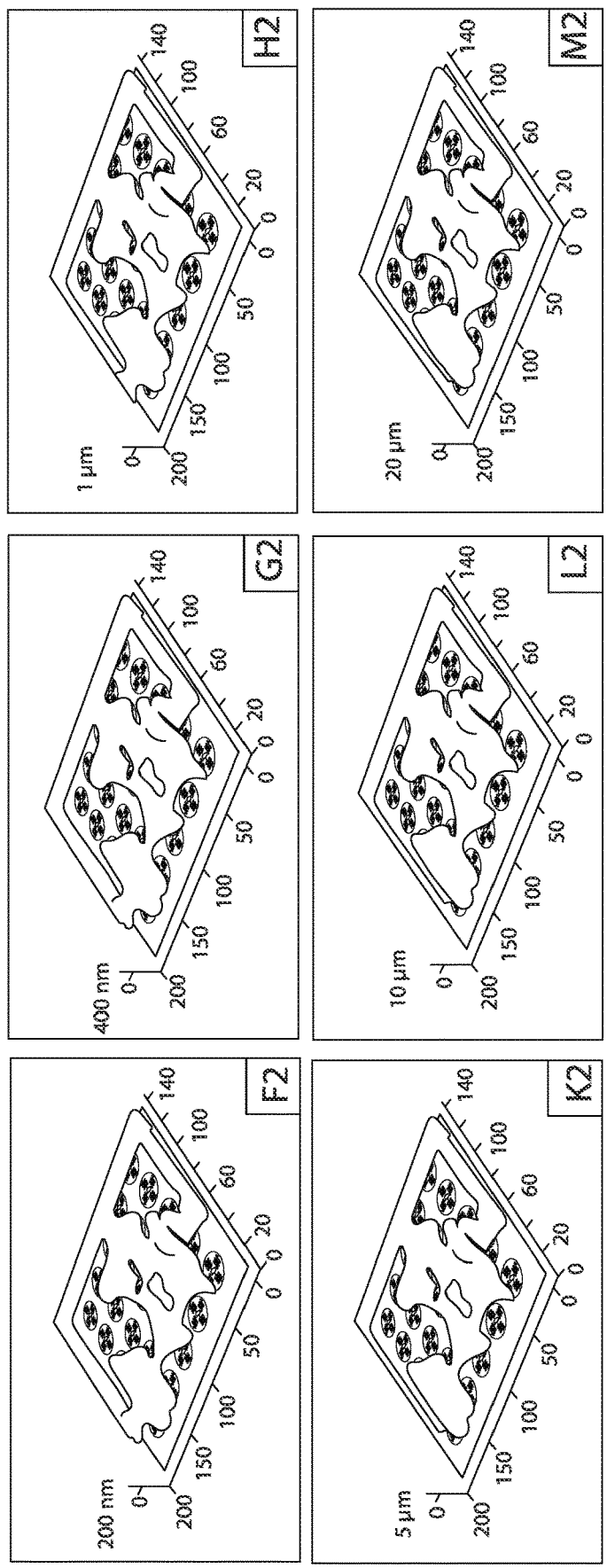

FIG. 3:

FIG. 3 shows 3D DEM images for different displacement states of the NiTi sensor element shown in FIG. 2A.

A suitable, sensitive optical readout system was designed and tested. Here, in initial measurements, a combination of off-axis digital holography (DHM) and digital image correlation (DIC) was used to record in-plane (DIC) and out-of-plane (DHM) displacements up to 200 nm for traction force measurement. Out-of-plane displacements are shown in FIG. 3 as an example for a NiTi sensor element.

Figure 4:
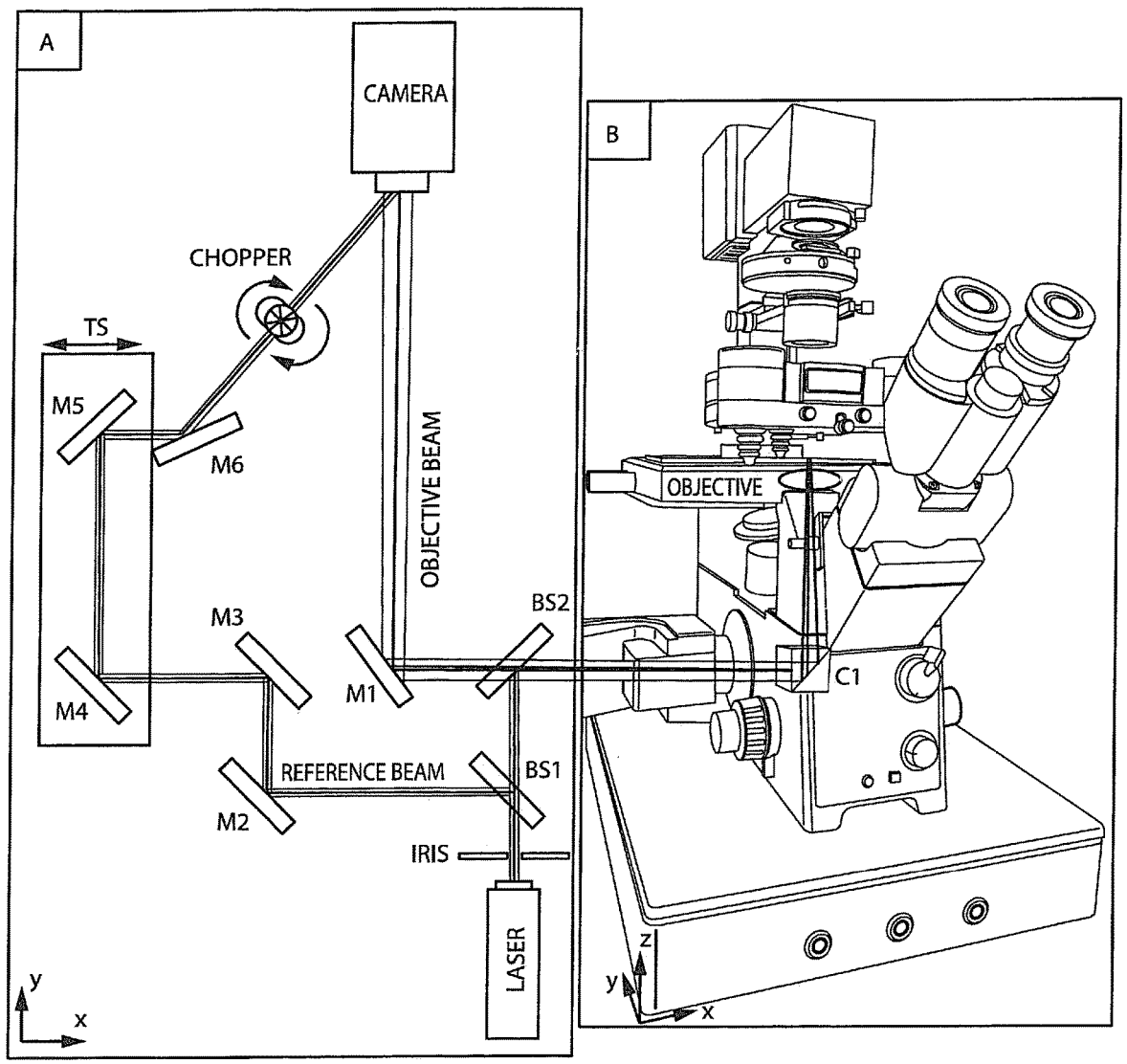

FIG. 4:

FIG. 4 shows a schematic representation of a DHM/DIC setup (A), which serves as an example as an add-on setup in combination with an AFM (B) for local and global 3D force measurement of cells. BS1 and BS2 are beam splitters, M1 to M6 are mirrors, C1 is an optical cube for coupling objective beam into inverted microscope. The chopper is required to block the reference beam for recording laser microscopic images of the sensor element for further digital image correlation and in-plane force measurement.

For future applications, the DHM/DIC adhesive force sensor system (see FIG. 4A) can be combined as an add-on application with other setups such as atomic force microscopes (AFM, see FIG. 4B), as shown schematically in FIG. 4. Here, sensor element displacements can be detected by DHM/DIC adjustment from the underside of the elements positioned above the objective on the inverted microscope sample holder, while a cell attached to the sensor array can be manipulated via the cantilever of an AFM head above. This arrangement would allow, for example, local force measurements via the DHM/DIC and global force measurements from above.

The invention claimed is:

1. A force measuring plate having a planar, regular arrangement of force measuring cells, each force measuring cell being formed in a hole in the force measuring plate, wherein for each force measuring cell exactly one planar element which is secured by springs in a self-supporting fashion is arranged and aligned parallel to the planar, regular arrangement of force measuring cells, each spring materially joined at a first end with an edge of a hole and at a second end to an edge of a planar element, wherein
   a. the force measuring plate, the springs and the planar elements are made of the same material,
   b. the springs are elongated meander structures with more than two meander periods,
   c. each planar element is surrounded by four rotationally symmetrical positioned springs, and d. each planar element is elastically deflectable in three spatial directions under the action of a force, with deflection and force being in a linear relationship.

2. A force measuring plate according to claim 1, wherein the structural thickness of planar elements and springs is less than 500 nanometers or less than 200 nanometers.

3. A force measuring plate according to claim 1, wherein the structural width of the meanders is less than 2 micrometers.

4. A force measuring plate according to claim 1, wherein the diameter of the force measuring cells is less than 200 microns.

5. A force measuring plate according to claim 1, wherein the force measuring plate is a biocompatible material.

6. A force measuring plate according to claim 1, wherein the arrangement of the force measuring cells is aligned along two axes which are perpendicular to one another.

7. A force measuring plate according to claim 6, wherein the elongate meander structures are aligned along the same axes that define the arrangement of the force measuring cells.

8. A force measuring plate according to claim 1, wherein the hole in the force measuring plate associated with a force measuring cell is circular.

9. A force measuring plate according to claim 1, wherein the planar elements are mirrored on a predetermined flat side.

10. A force measuring plate according to claim 9, wherein the mirror is a mirror coating, and wherein the planar elements have a functional layer on the flat side opposite the mirror coating.

11. A force measuring plate according to claim 1, wherein the material of the force measuring plate has a modulus of elasticity in the interval from 1 to 80 GPa.

12. A force measuring plate according to claim 1, wherein the diameters of the holes in the force measuring disc plate are in a ratio of 10:1 to the diameters of the planar elements.

13. A device for determining forces in the pico-Newton to nano-Newton range comprising at least one force measuring plate according to claim 1 and also having means for optically measuring three-dimensional deflections of the planar elements of the at least one force measuring plate.

14. The device according to claim 13, having an electronic translation device designed to determine the forces acting on the planar elements from the measured deflections.

15. A force measuring plate according to claim 1, wherein the force measuring plate is nickel-titanium alloy.

16. A force measuring plate according to claim 1, wherein the force measuring plate is amorphous silicon.

* * * * *